United States Patent [19]

Ekrann et al.

[11] Patent Number: 4,751,842

[45] Date of Patent: Jun. 21, 1988

[54] MEANS AND METHOD FOR MEASURING A MULTI-PHASE DISTRIBUTION WITHIN A FLOWING PETROLEUM STREAM

[75] Inventors: Steinar Ekrann, Stavanger; Arild Boe, Forus; Frank Schmidt, Stavanger; Endre Jacobsen, Sola; Rune W. Time, Bryne; Harald Vatne, Narbo, all of Norway

[73] Assignee: Texaco Inc., White Plains, N.Y.

[21] Appl. No.: 337

[22] Filed: Jan. 5, 1987

[51] Int. Cl.[4] .............................................. G01N 15/00
[52] U.S. Cl. ............................... 73/61.1 R; 73/861.04; 324/61 R
[58] Field of Search ............. 73/61.1 R, 61 R, 861.04, 73/861.08; 324/61 R, 61 P

[56] References Cited

U.S. PATENT DOCUMENTS

| | | | |
|---|---|---|---|
| 2,438,550 | 3/1948 | Ertzman | 324/61 R |
| 3,635,082 | 1/1972 | Prellwitz et al. | 324/61 R |
| 4,240,028 | 12/1980 | Davis, Jr. | 324/61 R |
| 4,266,188 | 5/1981 | Thompson | 324/61 R |
| 4,273,204 | 6/1981 | Gillen | 73/862.64 |
| 4,509,366 | 4/1985 | Matsushita et al. | 73/861.04 |
| 4,658,208 | 4/1987 | Lee et al. | 73/61 R |

*Primary Examiner*—Stewart J. Levy
*Assistant Examiner*—Hezron E. Williams
*Attorney, Agent, or Firm*—Robert A. Kulason; James J. O'Loughlin; Ronald G. Gillespie

[57] ABSTRACT

A petroleum stream measurement system includes a cell made of non-conductive material for passing a flowing petroleum stream. First and second sensors, spatially arranged with the cell and spaced at a predetermined distance apart, sense the capacitance of the petroleum stream and provides representative signals. A third sensor senses the capacitance of the petroleum stream and provides a corresponding signal. A fourth sensor senses the capacitance of the petroleum stream and provides a signal corresponding thereto. Apparatus receiving the signals from all the sensors derives the distribution of the different fluids within the petroleum stream.

15 Claims, 2 Drawing Sheets

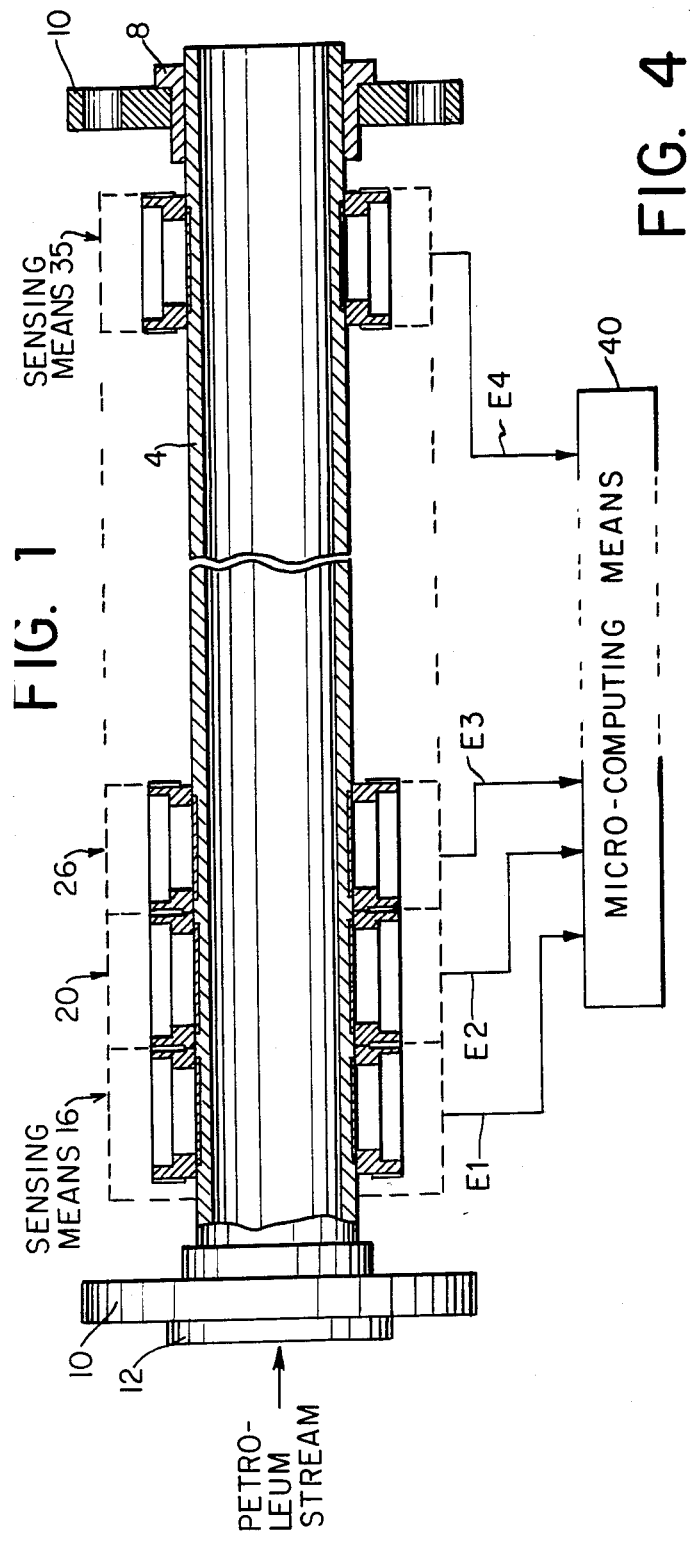
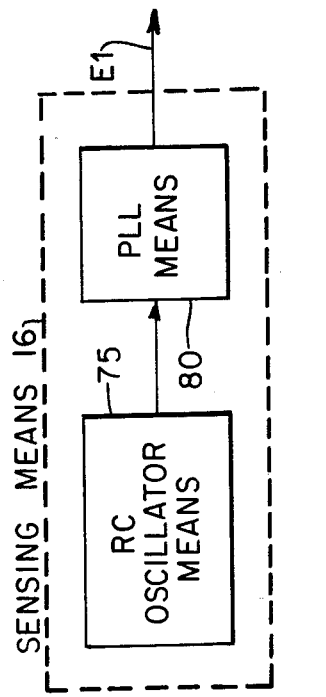

MEANS AND METHOD FOR MEASURING A MULTI-PHASE DISTRIBUTION WITHIN A FLOWING PETROLEUM STREAM

BACKGROUND OF THE INVENTION

FIELD OF THE INVENTION

The present invention relates to measurement systems and methods in general and, more particularly, to measurement systems and methods for measuring the phases of a petroleum stream.

SUMMARY OF THE INVENTION

A petroleum stream measurement system includes a cell made of non-conductive material for passing a flowing petroleum stream. First and second sensors, spatially arranged with the cell and spaced at a predetermined distance apart, sense the capacitance of the petroleum stream and provides representative signals. A third sensor senses the capacitance of the petroleum stream and provides a corresponding signal. A fourth sensor senses the capacitance of the petroleum stream and provides a signal corresponding thereto. Apparatus receiving the signals from all the sensors derives the distribution of the different fluids within the petroleum stream.

The objects and advantages of the invention will appear more fully hereinafter, from a consideration of the detailed description which follows, taking together the accompanying drawings, where one embodiment is illustrated by way of example. It is to be expressly understood, however, that the drawings are for illustrative purposes only, and are not to be construed as defining the limits of the invention.

DESCRIPTION OF THE DRAWINGS

FIG. 1 shows a petroleum stream measurement system, constructed in accordance with the present invention, partially in assembly form and partially in simplified block diagram form.

FIGS. 3A, 3B and 3C show different configurations of capacitor plates for the sensing means shown in FIG. 1.

FIG. 4 is a simplified block diagram of a sensing means shown in FIG. 1.

DESCRIPTION OF THE INVENTION

Figure 2:
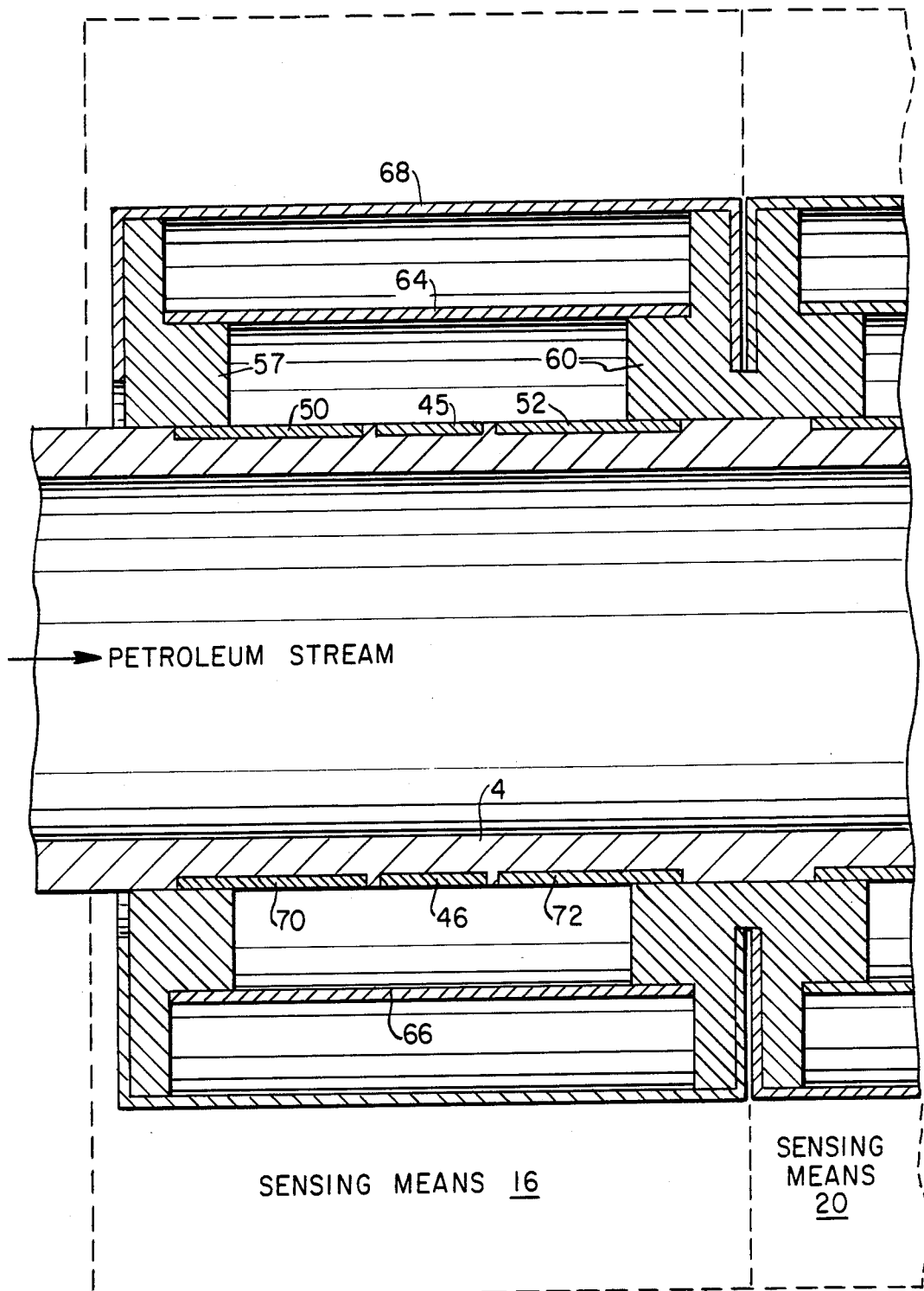
FIG. 2 shows a more detailed assembly type drawing of a sensing means shown in FIG. 1.

With reference to FIG. 1, a measurement cell 4 is made of non-conductive material such as plastic, designed so that it can be an integral part of a pipeline carrying a petroleum stream which may be gas, oil and water intercombined. Monitor cell 4 has fittings 8, 10 and 12 affixed to it for connection with a pipeline (not shown). Capacitive sensing means 16, 20, 26 and 35 are located on the monitoring cell 4 which provides signals E1, E2, E3 and E4, respectively, representative of the capacitance of the petroleum stream as it flows through monitor cell 4 as hereinafer explained. Signals E1 through E4 are provided to microcomputing means 40.

With reference to FIG. 2, there is shown in detail the sensor portion of sensing means 16. All of the sensing means are the same except for the arrangement of the capacitor plates which will be described more fully hereinafter. Measurement cell 4 has three grooves in it for each sensing means. Electrodes 45 and 46 are laid in the center groove and are connected to electronics described in detail hereinafter, but not shown in FIG. 2. Further, electrodes 45 and 46 are separated from each other and there is no conductivity between them. Guards 50, 52, 70, 72 are located in the two other grooves. A protective non-conductive covering of fiberglass tape may be provided to hold the electrodes 45, 46 and guards 50, 52, 70, 72 in place and to protect them from a harsh environment. Electrode 45, guards 50 and 52 are maintained at a signal ground potential. That is, the amplitudes of signals E1 through E4, are with reference to signal ground. Guards 70 and 72 are held at the same potential as electrode 46. Also mounted on monitoring cell 4 are mounting blocks 57 and 60. It is obvious that mounting block 57 is used at the end of a series of sensing means, while mounting block 60 is used internal in the series of sensing means 16 through 26. It should be noted that sensing means 35 utilizes only mounting blocks 57. The purpose of mounting blocks 57 and 60 is to support shielding around the capacitor electrodes 45 and 46. In this regard shield 64 is maintained at the signal ground potential and provides shielding and shield 66 is maintained at the potential of electrode 46. Further, another shield 68 is maintained at an environmental ground such as the pipeline ground to reduce noise on the pipeline from affecting the measurements.

With reference to FIGS. 3A, 3B and 3C, there is shown different arrangements of the capacitor plates of sensing means 16, 20 and 26.

With regards to FIG. 3A and FIG. 3B, the capacitor plates are substantially the same except Figure B differs by 90° in relationship to FIG. 3A. FIG. 3C represents yet another configuration sensing means 20.

In this example sensing means 35 will use the same configuration as sensing means 16 but must be spaced a known distance from sensing means 16. This results in signal E4 differing from signal E1 by a time factor related to velocity of the petroleum stream.

With reference to FIG. 4, sensing means 16 includes a conventional type RC oscillator means 75 which provides an output signal to phase lock loop means 80. Phase lock loop means 80 provides a pulse signal having a repetition rate corresponding to the frequency of the output signal from the RC oscillator means 75. The capacitor for RC oscillator means 75 is formed with the electrodes 45 and 46, mounted on monitor cell 4 with the petroleum stream flowing between electrodes 45 and 46. The resistor (not shown) has a known resistance value therefore the signal provided by RC oscillator means 75 is related to the capacitance of the dielectric between electrodes 45 and 46. Variance of the dielectric constant of the petroleum stream flowing through monitor cell 4 results in a corresponding change in frequency of the oscillator means 75 signal. As the petroleum stream flows between the various capacitor plates, slugs of gas, bubbles of gas, more water, less water and so forth will alter the capacitance between the capacitor plates causing signal E1 to vary accordingly.

It should be noted in an example just given, that sensing means 16 and sensing means 35 have their plates arranged in the same spatial manner but a predetermined distance apart so that the velocity of the stream can now be determined in accordance with the time difference between signals E1 and E4. Microcomputing means 40 is of a conventional type utilizing a microprocessor with associated memory. Stored in the memories are look-up tales for the various values of capacitance associated with different fluid distribution within measurement cell 4. The percent volume of water, gas and oil may be determined using the 'look up table memory'.

The measurement system and method of the present invention can provide qualitative information such as capacitance vs. time traces on a graph. The present invention can measure velocity and length of liquid slugs. The apparatus of the present invention, for each point of time, can measure approximate cross-sectional fluid distribution, which in turn leads a determination of volume fractions and hold-ups. Further the system and method of the present invention can determine the flow regime of a petroleum stream from the measured cross-sectional distributions and their time evolution. The present invention can also measure the flow rates of the individual fluids for some flow regimes.

A hold-up is defined as the area of the liquid divided by the area of the pipe.

Finally, it is noted that the present invention as hereinbefore described is a nonintrusive petroleum stream monitor. That is sensing means 16, 20 and 26 as shown in FIG. 1 do not intrude into the flow of the petroleum stream.

What is claimed is:

1. A petroleum stream measurement system comprising:
    cell means made of non-conductive material for passing a flowing petroleum stream,
    first and second sensing means spatially arranged wiith the cell means and spaced a predetermined distance apart for sensing the capacitance of the petroleum stream and providing signals representative thereof,
    third sensing means spatially arranged with the cell means for sensing the capacitance of the petroleum stream and providing a corresponding signal,
    fourth sensing means spatially arranged with the cell means for sensing the capacitance of the petroleum stream and providing a signal corresponding thereto, and
    means connected to all the sensing means for deriving the distribution of different fluids within the petroleum stream in accordance with all the sensed capacitances.

2. A system as described in claim 1 in which each sensing means includes:
    a pair of electrode means for acting as a capacitor,
    means spatially arranged with each electrode means for shielding the electrode means,
    oscillator means connected to both electrode means for providing a signal whose frequency is related to the capacitance of the petroleum stream passing through the electrode means, and
    phase lock loop means connected to the oscillator means for providing pulse signals in accordance with the signal from the oscillator means whose pulse repetition rate is related to the sensed capacitance.

3. A system as described in claim 2 in which the electrode means of the first and second sensing means are substantially the same size and configuration.

4. A system as described in claim 3 in which the third sensing means has electrode means which are substantially the same size as the electrode means of the first and second sensing means but have a substantially 90° displacement from the configuration from the electrode means of the first and second sensing means.

5. A system as described in claim 4 in which the fourth sensing means has one electrode means substantially larger than the other electrode means.

6. A petroleum stream measurement method comprising the steps of:
    flowing a petroleum stream through a cell made of non-conductive material,
    sensing the capacitances of thepetroleum stream and providing signals representative with first and second sensors spatially arranged with the cell and spaced a predetermined distance apart and providing signals representative of the sensed capacitances.
    sensing a capacitance of the petroleum stream and providing a corresponding signal with a third sensor spatially arranged with the cell,
    sensing a capacitance of the petroleum stream and providing a signal corresponding thereto with a fourth sensor spatially arranged with the cell, and
    deriving the distribution of different fluids within the petroleum stream.

7. A method as described in claim 6 in which each sensing step includes:
    arranging a pair of electrodes so that the petroleum stream flows between the electrodes,
    shielding the electrodes,
    providing a signal whose frequency is related to the capacitance of the petroleum stream passing between the electrodes, and
    providing pulse signals whose pulse repetition rate is related to the sensed capacitance.

8. A method as described in claim 7 in which the sensing step includes:
    using two electrodes of substantially the same size and configuration in the first and second sensors.

9. A method as described in claim 8 in which the sensing step includes:
    using two electrodes having the same size in the third sensor but at a substantially 90° displacement from the configuration of the electrodes of the first and second sensors.

10. A method as described in claim 9 in which the sensing step includes:
    using two electrodes with the fourth sensor, with one electrode being substantially larger than the other electrode.

11. A petroleum stream measurement system comprising:
    cell means made of non-conductive material for passing a flowing petroleum stream,
    first and second sensing means spatially arranged with the cell means so as not to intrude into the flow of the petroleum stream and spaced a predetermined distance apart for sensing the capacitance of the petroleum stream and providing signals representative thereof,
    third sensing means spatially arranged with the cell means so as not to intrude into the flow of the petroleum stream for sensing the capacitance of the petroleum stream and providing a corresponding signal,
    fourth sensing means spatially arranged with the cell means so as not to intrude into the flow of the petroleum stream for sensing the capacitance of the petroleum stream and providing a signal corresponding thereto, and
    means connected to all the sensing means for deriving the distribution of different fluids within the petroleum stream in accordance with all the sensed capacitances.

12. A system as described in claim 11 in which each sensing means includes:
   a pair of electrode means for acting as a capacitor,
   means spatially arranged with each electrode means for shielding the electrode means,
   oscillator means connected to both electrode means for providing a signal whose frequency is related to the capacitance of the petroleum stream passing through the electrode means, and
   phase lock loop means connected to the oscillator means for providing pulse signals in accordance with the signal from the oscillator means whose pulse repetition rate is related to the sensed capacitance.

13. A system as described in claim 12 in which the electrode means of the first and second sensing means are substantially the same size and configuration.

14. A system as described in claim 13 in which the third sensing means has electrode means which are substantially the same size as the electrode means of the first and second sensing means but have a substantially 90° displacement from the configuration from the electrode means of the first and second sensing means.

15. A system as described in claim 14 in which the fourth sensing means has one electrode means substantially larger than the other electrode means.

* * * * *